United States Patent
Rickard (10) Patent No.: US 8,545,431 B2
(45) Date of Patent: Oct. 1, 2013

(54) LUMEN CLEARING VALVE FOR GLAUCOMA DRAINAGE DEVICE

(75) Inventor: Matthew J. A. Rickard, Tustin, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 634 days.

(21) Appl. No.: 12/609,043

(22) Filed: Oct. 30, 2009

(65) Prior Publication Data

US 2011/0071456 A1 Mar. 24, 2011

Related U.S. Application Data

(63) Continuation-in-part of application No. 12/563,244, filed on Sep. 21, 2009, now Pat. No. 8,257,295.

(51) Int. Cl.
*A61M 5/00* (2006.01)
(52) U.S. Cl.
USPC .................................. 604/9; 604/8
(58) Field of Classification Search
USPC .............................. 604/8–10, 294
See application file for complete search history.

(56) References Cited

U.S. PATENT DOCUMENTS

| | | | |
|---|---|---|---|
| 4,089,329 A | 5/1978 | Couvillon et al. | |
| 4,206,762 A | 6/1980 | Cosman | |
| 4,457,757 A | 7/1984 | Molteno | |
| 4,656,827 A | 4/1987 | Puillet | |
| 4,750,901 A | 6/1988 | Molteno | |
| 4,869,282 A | 9/1989 | Sittler et al. | |
| 4,922,913 A | 5/1990 | Waters et al. | |
| 5,005,577 A | 4/1991 | Frenkel | |
| 5,083,742 A | 1/1992 | Wylie et al. | |
| 5,178,604 A | 1/1993 | Baerveldt | |
| 5,179,953 A | 1/1993 | Kursar | |
| 5,397,300 A | 3/1995 | Baerveldt | |
| 5,466,233 A | 11/1995 | Weiner et al. | |

(Continued)

FOREIGN PATENT DOCUMENTS

DE 4438201 5/1996
EP 2427097 3/2012

(Continued)

OTHER PUBLICATIONS

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 466- 469, Lyon, France.

(Continued)

*Primary Examiner* — Philip R Wiest
(74) *Attorney, Agent, or Firm* — Kenneth Bassinger (57) ABSTRACT

A glaucoma drainage device has a housing with an open outlet end. A tube is in fluid communication with the housing. An actuator is located in the housing. An actuation arm is located at least partially in the housing and is coupled to the actuator. A tapered arm is rigidly coupled to the actuation arm. A needle head is located opposite the tapered arm. A tapered end of the tapered arm is located at least partially in the tube. When the tapered arm is moved, it can clear an obstruction from the tube. When the needle head is moved, it can disperse aqueous or clear fibers from the drainage location.

26 Claims, 8 Drawing Sheets

(56) References Cited

U.S. PATENT DOCUMENTS

| | | | |
|---|---|---|---|
| 5,476,445 A | 12/1995 | Baerveldt | |
| 5,558,629 A | 9/1996 | Baerveldt | |
| 5,573,646 A | 11/1996 | Saito et al. | |
| 5,626,558 A | 5/1997 | Suson | |
| 5,681,275 A | 10/1997 | Ahmed | |
| 5,707,643 A | 1/1998 | Ogura et al. | |
| 5,910,110 A | 6/1999 | Bastable | |
| 6,007,511 A | 12/1999 | Prywes | |
| 6,048,328 A | 4/2000 | Haller et al. | |
| 6,251,090 B1 | 6/2001 | Avery et al. | |
| 6,447,449 B1 | 9/2002 | Fleischman et al. | |
| 6,468,283 B1* | 10/2002 | Richter et al. | 606/108 |
| 6,579,235 B1 | 6/2003 | Abita et al. | |
| 6,589,198 B1 | 7/2003 | Soltanpour et al. | |
| 6,682,500 B2 | 1/2004 | Soltanpour et al. | |
| 6,712,764 B2 | 3/2004 | Jeffries et al. | |
| 6,719,750 B2 | 4/2004 | Varner et al. | |
| 6,749,568 B2 | 6/2004 | Fleischman et al. | |
| 6,939,299 B1* | 9/2005 | Petersen et al. | 600/398 |
| 6,976,982 B2 | 12/2005 | Santini, Jr. et al. | |
| 7,137,952 B2 | 11/2006 | Leonardi et al. | |
| 7,169,106 B2 | 1/2007 | Fleischman et al. | |
| 7,252,006 B2 | 8/2007 | Tai et al. | |
| 7,354,416 B2 | 4/2008 | Quiroz-Mercado et al. | |
| 7,409,863 B2 | 8/2008 | Bateman et al. | |
| 7,612,328 B2 | 11/2009 | Kaiser | |
| 7,756,559 B2 | 7/2010 | Abreu | |
| 7,824,699 B2 | 11/2010 | Ralph et al. | |
| 8,182,435 B2 | 5/2012 | Dacquay et al. | |
| 8,257,295 B2 | 9/2012 | Rickard et al. | |
| 8,419,673 B2 | 4/2013 | Rickard | |
| 2001/0000527 A1 | 4/2001 | Yaron et al. | |
| 2002/0019607 A1 | 2/2002 | Bui | |
| 2002/0049374 A1 | 4/2002 | Abreu | |
| 2002/0087111 A1 | 7/2002 | Ethier et al. | |
| 2002/0099359 A1 | 7/2002 | Santini, Jr. et al. | |
| 2002/0139947 A1 | 10/2002 | Wang | |
| 2002/0143284 A1 | 10/2002 | Tu et al. | |
| 2002/0193674 A1 | 12/2002 | Fleischman et al. | |
| 2003/0014036 A1 | 1/2003 | Varner et al. | |
| 2003/0078487 A1 | 4/2003 | Jeffries et al. | |
| 2003/0225318 A1 | 12/2003 | Montegrande et al. | |
| 2004/0013702 A1 | 1/2004 | Glover | |
| 2004/0059248 A1 | 3/2004 | Messner et al. | |
| 2004/0073137 A1 | 4/2004 | Lloyd et al. | |
| 2004/0111050 A1 | 6/2004 | Smedley et al. | |
| 2004/0116794 A1 | 6/2004 | Fink et al. | |
| 2004/0186367 A1 | 9/2004 | Fresco | |
| 2004/0254438 A1 | 12/2004 | Chuck et al. | |
| 2004/0254517 A1* | 12/2004 | Quiroz-Mercado et al. | 604/8 |
| 2005/0159660 A1 | 7/2005 | Montegrande et al. | |
| 2005/0271704 A1 | 12/2005 | Tu et al. | |
| 2005/0273033 A1 | 12/2005 | Grahn et al. | |
| 2006/0131350 A1 | 6/2006 | Schechter et al. | |
| 2007/0019156 A1 | 1/2007 | Fink | |
| 2007/0032757 A1 | 2/2007 | Medow et al. | |
| 2007/0077270 A1 | 4/2007 | Wen | |
| 2007/0109117 A1 | 5/2007 | Heitzmann et al. | |
| 2007/0123767 A1 | 5/2007 | Montegrande et al. | |
| 2007/0129623 A1 | 6/2007 | Fleischman et al. | |
| 2007/0212397 A1 | 9/2007 | Roth | |
| 2008/0015421 A1 | 1/2008 | Penner | |
| 2008/0027478 A1 | 1/2008 | Connors et al. | |
| 2008/0077127 A1 | 3/2008 | Gao et al. | |
| 2008/0097276 A1 | 4/2008 | Bertrand et al. | |
| 2008/0125691 A1 | 5/2008 | Yaron et al. | |
| 2008/0129486 A1 | 6/2008 | Jeckelmann et al. | |
| 2008/0147021 A1 | 6/2008 | Jani | |
| 2008/0228127 A1* | 9/2008 | Burns et al. | 604/9 |
| 2009/0069648 A1 | 3/2009 | Irazoqui et al. | |
| 2009/0076367 A1 | 3/2009 | Sit et al. | |
| 2009/0143713 A1 | 6/2009 | Van Dam et al. | |
| 2009/0227933 A1 | 9/2009 | Karageozian | |
| 2009/0240215 A1 | 9/2009 | Humayun et al. | |
| 2009/0275924 A1 | 11/2009 | Lattanzio et al. | |
| 2009/0312742 A1 | 12/2009 | Pang et al. | |
| 2010/0010416 A1 | 1/2010 | Juan, Jr. et al. | |
| 2010/0042209 A1 | 2/2010 | Guarnieri | |
| 2010/0121348 A1 | 5/2010 | Van Der Burg et al. | |
| 2010/0174272 A1 | 7/2010 | Weiner | |
| 2010/0222769 A1 | 9/2010 | Meng et al. | |
| 2010/0234717 A1 | 9/2010 | Wismer | |
| 2010/0253167 A1 | 10/2010 | Charnley et al. | |
| 2010/0305550 A1 | 12/2010 | Meng et al. | |
| 2011/0046536 A1 | 2/2011 | Stegmann et al. | |
| 2011/0071454 A1 | 3/2011 | Santos et al. | |
| 2011/0071459 A1 | 3/2011 | Rickard et al. | |
| 2011/0071505 A1 | 3/2011 | Rickard et al. | |
| 2011/0248671 A1 | 10/2011 | Santos et al. | |

FOREIGN PATENT DOCUMENTS

| | | |
|---|---|---|
| WO | 93/03665 | 3/1993 |
| WO | 9803809 | 1/1998 |
| WO | WO 98/03665 | 1/1998 |
| WO | WO 99/38470 A2 | 8/1999 |
| WO | WO 99/38470 A3 | 10/1999 |
| WO | WO 01/94784 | 12/2001 |
| WO | 02056758 | 7/2002 |
| WO | 03/001991 | 1/2003 |
| WO | WO 03/102632 | 12/2003 |
| WO | 2005088417 | 9/2005 |
| WO | 2007/136993 | 11/2007 |
| WO | WO 2007/127305 A2 | 11/2007 |
| WO | WO 2008/061043 A2 | 5/2008 |
| WO | 2008084350 | 7/2008 |
| WO | 2009010799 | 1/2009 |
| WO | 2009/026499 | 2/2009 |
| WO | 2009/049686 | 4/2009 |
| WO | WO 2009/081031 | 7/2009 |
| WO | 2010/129446 A1 | 11/2010 |
| WO | WO 2011/034727 A1 | 3/2011 |
| WO | WO 2011/034738 A1 | 3/2011 |
| WO | WO 2011/034740 A1 | 3/2011 |
| WO | WO 2011/034742 A2 | 3/2011 |
| WO | WO 2011/035218 A1 | 3/2011 |
| WO | WO 2011/034742 A3 | 5/2011 |
| WO | 2012012017 | 1/2012 |

OTHER PUBLICATIONS

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.

Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.

Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.

Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matted, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.

McLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.

Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.

Puers, Robert, "Linking Sensors with Telemetry: Impact on the System Design," in Proc. 8th Intl Conference of Solid State Sensors, Actuators, Eurosens, Jun. 25-29, 1995, pp. 169-174, Stockholm, Sweden.

Schnakenberg, U., et al, "Initial Investigations on Systems for Measuring Intraocular Pressure," Sensors and Actuators, 2000, p. 287-291, vol. 85, Elsevier Science B.V., Germany.

Stangel, Karsten, et al, "A Programmable Intraocular Cmos Pressure Sensor System Implant," IEEE Journal of Solid-State Circuits, Jul. 2001, pp. 1094-1100, vol. 36, No. 7, IEEE, Germany.

Ullerich, Stella, et al, "Micro Coils for an Advanced System for Measuring Intraocular Pressure," 1st Annual Intl IEEE-EMBS Special Topic Conference on Microtechnologies in Medicine & Biology, Oct. 12-14, 2000, pp. 470- 474, Lyon, France.

Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.

"Walter, Peter; Intraocular Pressure Sensor: Where Are We—Where Will We Go? Journal Grade's Archive for Clinical and Experimental Ophthalmology; Publisher Springer Berline/Heidelberg; ISSN 0721-832X (Print) 1435-702X (Online); Issue vol. 240, No. 5/May 2002 DOI 10.1007/s00417-002-0474-y; pp. 335-336; Subject Collection Medicine."

Byunghoon Bae, Hongseok Kee, Seonho Kim, Peon Lee, Taeseok Sim, Yongkweon Kim and Kyihwan Park; "In Vitro Experiment of the Pressure Regulating Valve for a Glaucoma Impact"; Journal of Micromechanics and Microengineering, 13 (2003); pp. 613-619.

International Searching Authority, Search Report and Written Opinion of the International Searching Authority, PCT/US2010/033329, Jul. 13, 2010, 14 pages.

International Searching Authority, Search Report and Written Opinion of the International Searching Authority, PCT/US2010/047600, Dec. 14, 2010, 13 pages.

International Searching Authority, Search Report and Written Opinion of the International Searching Authority, PCT/US2010/047429, Nov. 1, 2010, 15 pages.

International Searching Authority, Search Report and Written Opinion of the International Searching Authority, PCT/US2010/049424, Nov. 26, 2010, 15 pages.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

International Searching Authority, Written Opinion of the International Searching Authority, PCT/US2010/047605, Dec. 16, 2010, 9 pages.

International Searching Authority, Search Report of the International Searching Authority, PCT/US2011/036742, Aug. 17, 2011, 2 pages.

Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.

Neagu Cristina R.; "A Medical Microactuator Based on an Electrochemical Principle"; Thesis at the Twente University,the Netherlands, Enschede; Aug. 28, 1998; pp. 1-162.

Saloomeh Saati MD., Ronalee Lo PhD, Po-Ying Li PhD, Ellis Meng PhD, Rohit Varma MD MPH, and Mark S. Humayun MD PhD; "Mini Drug Pump for Ophthalmic Use"; TRANS Am Ophthalmol Soc 2009; 107; pp. 60-71.

Erik Stemme and Goran Stemme; "A Valveless Diffuser/Nozzle-Based Fluid Pump"; ScienceDirect; Sensors and Actuators A, 39 (1993); pp. 159-167.

International Searching Authority, International Search Report of the International Searching Authority, PCT/US2010/047612, Dec. 21, 2010, 7 pages.

International Searching Authority, Written Opinion of the International Searching Authority, PCT/US2010/047612, Dec. 21, 2010, 10 pages.

International Searching Authority, International Search Report, PCT/US2013/026066, Apr. 17, 2013, 5 pages.

International Searching Authority, Written Opinion of the International Searching Authority, PCT/US2013/026066, Apr. 17, 2013, 8 pages.

International Searching Authority, Invitation to Pay Additional Fees and, Where Applicable, Protest Fee (Partial Search Report attached), PCT/US2012/067741, Apr. 2, 2013, 6 pages.

Driot et al.; "Ocular pharmacokinetics of fluocinolone acetonide after RetisertTM intravitreal implantation in rabbits over a 1-year period"; J. Ocular Pharm; 20; 3;pp. 269-275.

Glybina et al.; "Neuroprotective properties of fluocinolone acetonide chronically delivered into the vitreous of albino RCS rats"; IVOS; 47; ARVO e-Abstract 1028.

Kuppermann B D et al., 2006, "Efficacy and safety of a novel intravitreous dexamethasone drug-delivery system after applicator or incisional placement in patients with macular edema", IOVS, 47 ARVO E-Abs 5913.

Miyamoto H et al., 1997, Biodegradable scleral implant for intravitreal controlled release of fluconazole, Curr Eye Res, 16(9), 930-935.

Mruthyunjaya P et al., 2003, "An intravitreal sustained release fluocinolone acetonide device to treat severe experimental uveitis", IOVS, 44, ARVO E-Abs 4215.

Ratanapakorn T et al., 2005, "Helical intravitreal triamcinolone implant: An explanation survival study", IVOS 46 E-Abs 484.

Rego MGR et al., 2004, "In vitro evaluation of sustained-release intravitreal dexamethasone implants", IOVS, 45 E-Abs 5060.

Sakurai E et al., 2001, "Scleral plug of biodegradable polymers containing ganciclovir for experimental cytomegalovirus retinitis", IOVS, 42(9), 2043-2048.

See R F et al., 2006, "Safety and drug release profile of injectable intravitreal sustained-release fluocinolone acetonide device", IOVS, 47, ARVO E-Abs 5119.

Tano R et al., 2005, Helical intravitreal implant: surgical method development and outcomes, IOVS, 46, ARVO E-Abs 483.

Varner S E et al., 2003, "Development of a minimally invasive intravitreal implant for drug delivery", IOVS, 44, ARVO E-Abs 4214.

Weiner A L, 2007, "Drug Delivery Systems in Ophthalmic Applications, in: Ocular Therapeutics; Eye on New Discoveries; T. Yorio, A. Clark, M.Wax, Eds, Elsevier Press/Academic Press, New York", pp. 7-43.

Yasukawa T et al., 2001, "Biodegradable scleral plugs for vitreoretinal drug delivery", Adv. Drug Del Rev., 52(1), 25-36.

International Searching Authority, International Search Report, PCT/US2012/068878, Mar. 3, 2013, 5 pages.

International Searching Authority, International Search Report, PCT/US2012/067747, Apr. 2, 2013, 4 pages.

International Searching Authority, Written Opinion of the International Searching Authority, PCT/US2012/067747, Apr. 2, 2013, 7 pages.

* cited by examiner

LUMEN CLEARING VALVE FOR GLAUCOMA DRAINAGE DEVICE

This application is a continuation-in-part of U.S. application Ser. No. 12/563,244 filed Sep. 21, 2009 now U.S. Pat. No. 8,257,295.

BACKGROUND OF THE INVENTION

The present invention relates to a glaucoma drainage device with an active, reciprocating member that acts to clear the lumen, prevent fibrosis, and/or properly disperse aqueous.

Glaucoma, a group of eye diseases affecting the retina and optic nerve, is one of the leading causes of blindness worldwide. Glaucoma results when the intraocular pressure (IOP) increases to pressures above normal for prolonged periods of time. IOP can increase due to an imbalance of the production of aqueous humor and the drainage of the aqueous humor. Left untreated, an elevated IOP causes irreversible damage the optic nerve and retinal fibers resulting in a progressive, permanent loss of vision.

The eye's ciliary body epithelium constantly produces aqueous humor, the clear fluid that fills the anterior chamber of the eye (the space between the cornea and iris). The aqueous humor flows out of the anterior chamber through the uveoscleral pathways, a complex drainage system. The delicate balance between the production and drainage of aqueous humor determines the eye's IOP.

Open angle (also called chronic open angle or primary open angle) is the most common type of glaucoma. With this type, even though the anterior structures of the eye appear normal, aqueous fluid builds within the anterior chamber, causing the IOP to become elevated. Left untreated, this may result in permanent damage of the optic nerve and retina. Eye drops are generally prescribed to lower the eye pressure. In some cases, surgery is performed if the IOP cannot be adequately controlled with medical therapy.

Only about 10% of the population suffers from acute angle closure glaucoma. Acute angle closure occurs because of an abnormality of the structures in the front of the eye. In most of these cases, the space between the iris and cornea is more narrow than normal, leaving a smaller channel for the aqueous to pass through. If the flow of aqueous becomes completely blocked, the IOP rises sharply, causing a sudden angle closure attack.

Secondary glaucoma occurs as a result of another disease or problem within the eye such as: inflammation, trauma, previous surgery, diabetes, tumor, and certain medications. For this type, both the glaucoma and the underlying problem must be treated.

Figure 1:
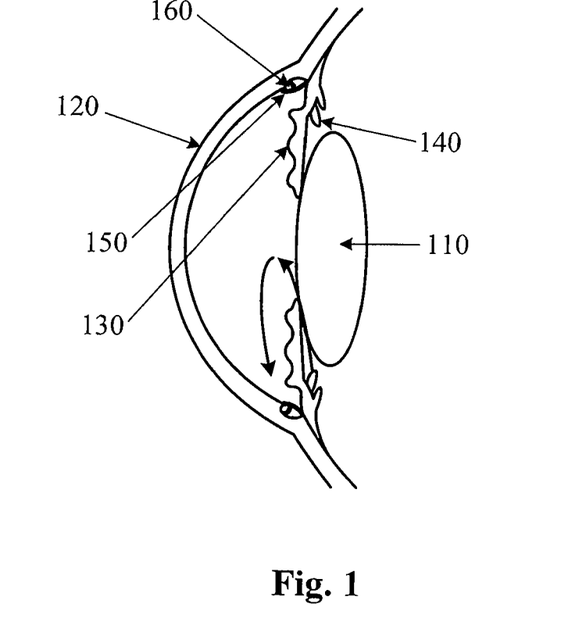
FIG. 1 is a diagram of the front portion of an eye.

FIG. 1 is a diagram of the front portion of an eye that helps to explain the processes of glaucoma. In FIG. 1, representations of the lens 110, cornea 120, iris 130, ciliary bodies 140, trabecular meshwork 150, and Schlemm's canal 160 are pictured. Anatomically, the anterior chamber of the eye includes the structures that cause glaucoma. Aqueous fluid is produced by the ciliary bodies 140 that lie beneath the iris 130 and adjacent to the lens 110 in the anterior chamber. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The first structure, and the one most commonly implicated in glaucoma, is the trabecular meshwork 150. The trabecular meshwork 150 extends circumferentially around the anterior chamber in the angle. The trabecular meshwork 150 seems to act as a filter, limiting the outflow of aqueous humor and providing a back pressure producing the IOP. Schlemm's canal 160 is located beyond the trabecular meshwork 150. Schlemm's canal 160 has collector channels that allow aqueous humor to flow out of the anterior chamber. The two arrows in the anterior chamber of FIG. 1 show the flow of aqueous humor from the ciliary bodies 140, over the lens 110, over the iris 130, through the trabecular meshwork 150, and into Schlemm's canal 160 and its collector channels.

In glaucoma patients, IOP can vary widely during a 24 hour period. Generally, IOP is highest in the early morning hours before medication is administered upon waking. Higher pressures damage the optic nerve and can lead to blindness. Accordingly, it would be desirable to measure IOP over time in order to assess the efficacy of various treatments. In addition, continuous IOP data can be used as part of a feedback mechanism to support an implanted active IOP-controlling system (e.g. valve or pump for controlling aqueous humor flow or delivering drugs). The present invention provides an IOP measuring device.

SUMMARY OF THE INVENTION

In one embodiment consistent with the principles of the present invention, the present invention is a glaucoma drainage device that has a housing with an open outlet end. A tube is in fluid communication with the housing. An actuator is located in the housing. An actuation arm is located at least partially in the housing and is coupled to the actuator. A tapered arm is rigidly coupled to the actuation arm. A tapered end of the tapered arm is located at least partially in the tube. In other aspects of the present invention, a needle head is located opposite the tapered arm. When the tapered arm is moved, it can clear an obstruction from the tube. When the needle head is moved, it can disperse aqueous or clear fibers from the drainage location.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 2:
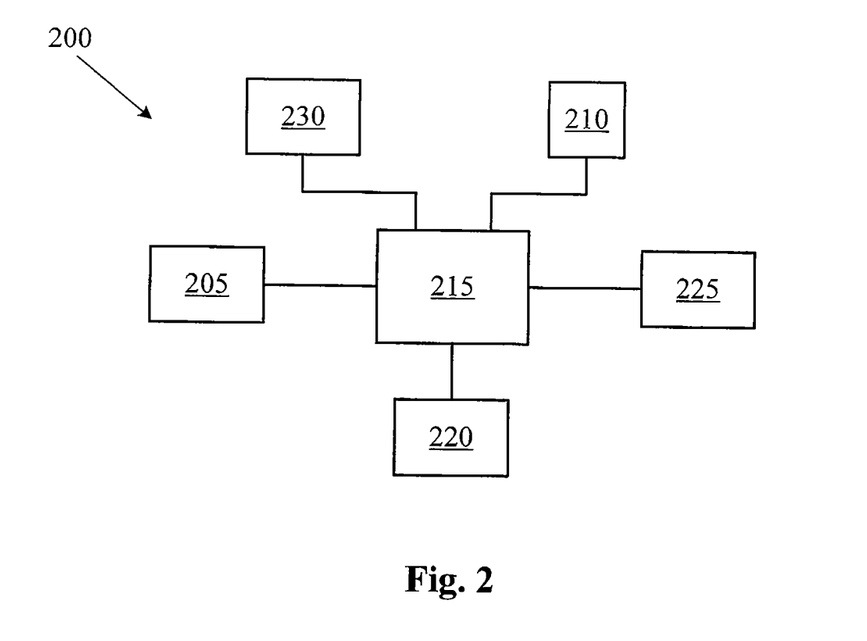
FIG. 2 is a block diagram of an IOP measuring system according to the principles of the present invention.

FIG. 2 is a block diagram of an IOP measuring system 200 according to the principles of the present invention. In FIG. 2, the IOP measuring system includes power source 205, IOP sensor 210 (which can include P1, P2, and/or P3), processor 215, memory 220, data transmission module 225, and optional speaker 230.

Power source 205 is typically a rechargeable battery, such as a lithium ion or lithium polymer battery, although other types of batteries may be employed. In addition, any other type of power cell is appropriate for power source 205. Power source 205 provides power to the system 200, and more particularly to processor 215. Power source can be recharged via an RFID link or other type of magnetic coupling.

Processor 215 is typically an integrated circuit with power, input, and output pins capable of performing logic functions. In various embodiments, processor 215 is a targeted device controller. In such a case, processor 215 performs specific control functions targeted to a specific device or component, such as a data transmission module 225, speaker 230, power source 205, or memory 220. In other embodiments, processor 215 is a microprocessor. In such a case, processor 215 is programmable so that it can function to control more than one component of the device. In other cases, processor 215 is not a programmable microprocessor, but instead is a special purpose controller configured to control different components that perform different functions.

Memory 220 is typically a semiconductor memory such as NAND flash memory. As the size of semiconductor memory is very small, and the memory needs of the system 200 are small, memory 220 occupies a very small footprint of system 200. Memory 220 interfaces with processor 215. As such, processor 215 can write to and read from memory 220. For example, processor 215 can be configured to read data from the IOP sensor 210 and write that data to memory 220. In this manner, a series of IOP readings can be stored in memory 220. Processor 215 is also capable of performing other basic memory functions, such as erasing or overwriting memory 220, detecting when memory 220 is full, and other common functions associated with managing semiconductor memory.

Data transmission module 225 may employ any of a number of different types of data transmission. For example, data transmission module 225 may be active device such as a radio. Data transmission module 225 may also be a passive device such as the antenna on an RFID tag. In this case, an RFID tag includes memory 220 and data transmission module 225 in the form of an antenna. An RFID reader can then be placed near the system 200 to write data to or read data from memory 220. Since the amount of data typically stored in memory 220 is likely to be small (consisting of IOP readings over a period of time), the speed with which data is transferred is not crucial. Other types of data that can be stored in memory 220 and transmitted by data transmission module 225 include, but are not limited to, power source data (e.g. low battery, battery defect), speaker data (warning tones, voices), IOP sensor data (IOP readings, problem conditions), and the like.

Optional speaker 230 provides a warning tone or voice to the patient when a dangerous condition exists. For example, if IOP is at a level that is likely to lead to damage or presents a risk to the patient, speaker 230 may sound a warning tone to alert the patient to seek medical attention or to administer eye drops. Processor 215 reads IOP measurements from IOP sensor 210. If processor 215 reads one or a series of IOP measurements that are above a threshold, then processor 215 can operate speaker 230 to sound a warning. The threshold can be set and stored in memory 220. In this manner, an IOP threshold can be set by a doctor, and when exceeded, a warning can be sounded.

Alternatively, data transmission module may be activated to communicate an elevated IOP condition to a secondary device such as a PDA, cell phone, computer, wrist watch, custom device exclusively for this purpose, remote accessible data storage site (e.g. an internet server, email server, text message server), or other electronic device. In one embodiment, a personal electronic device uploads the data to the remote accessible data storage site (e.g. an internet server, email server, text message server). Information may be uploaded to a remote accessible data storage site so that it can be viewed in real time, for example, by medical personnel. In this case, the secondary device may contain the speaker 230. For example, in a hospital setting, after a patient has undergone glaucoma surgery and had system 200 implanted, a secondary device may be located next to the patient's hospital bed. Since IOP fluctuations are common after glaucoma surgery (both on the high side and on the low side which is also a dangerous condition), processor 215 can read IOP measurements made by an implanted IOP sensor 210. If processor 215 reads an unsafe IOP condition, data transmission module 225 can alert the patient and medical staff via speaker 230 or by transmitting the unsafe readings to a secondary device.

Such a system is also suitable for use outside a hospital setting. For example, if an unsafe IOP condition exists, processor 215 can operate speaker 230 to sound an audible warning. The patient is then alerted and can seek medical attention. The warning can be turned off by a medical professional in a number of ways. For example, when data transmission module 225 is an RFID tag, an RFID link can be established between an external device and system 200. This external device can communicate with system 200 to turn off the speaker 230. Alternatively, an optical signal may be read by system 200. In this case, data transmission module 225 has an optical receptor that can receive a series of light pulses that represent a command—such as a command to turn off speaker 230.

Figure 3:
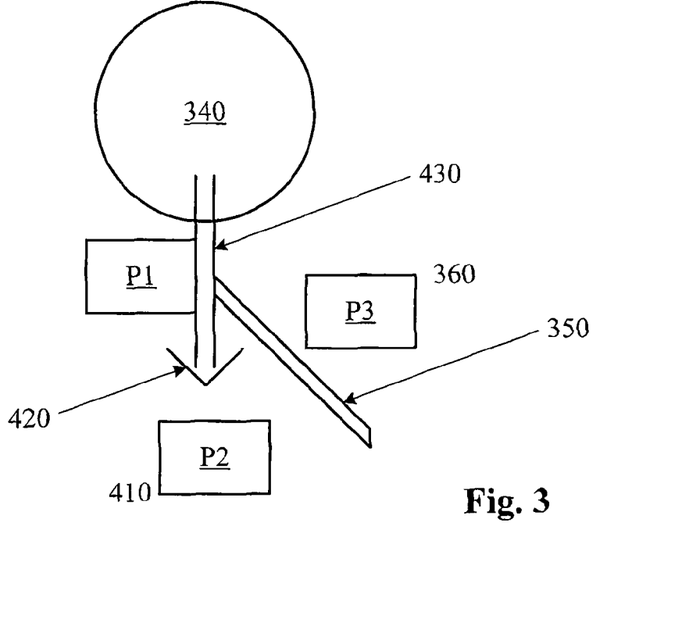
FIG. 3 is a diagram of an IOP sensor according to the principles of the present invention.

FIG. 3 is a diagram of an IOP sensor according to the principles of the present invention. In FIG. 3, the IOP sensor consists of three pressure sensors, P1, P2, and P3, a drainage tube 430, valve 420, and divider 350. Pressure sensor P1 is located in or is in fluidic communication with the anterior chamber 340, pressure sensor P2 is located at a drainage site in the subconjunctival space, and pressure sensor P3 is located remotely from P1 and P2. Pressure sensor P1 can also be located in a lumen or tube that is in fluid communication with the anterior chamber. As such, pressure sensor P1 measures a pressure in the anterior chamber, pressure sensor P2 measures a pressure at a drainage site, and pressure sensor P3 generally measures or corresponds to atmospheric pressure.

In FIG. 3, tube 430 drains aqueous from the anterior chamber 340 of the eye. A valve 420 controls the flow of aqueous through the tube 430. Pressure sensor P1 measures the pressure in the tube 430 upstream from the valve 420 and downstream from the anterior chamber 340. In this manner, pressure sensor P1 measures the pressure in the anterior chamber 340. The expected measurement discrepancy between the true anterior chamber pressure and that measured by P1 when located in a tube downstream of the anterior chamber (even when located between the sclera and the conjunctiva) is very minimal. For example, Poiseuille's law for pipe flow predicts a pressure drop of 0.01 mmHg across a 5-millimeter long tube with a 0.300 millimeter inner diameter for a flow rate of 3 microliters per minute of water.

A divider 350 separates pressure sensor P2 from pressure sensor P3. Pressure sensor P2 is located at a drainage site (e.g. 410 in FIG. 4). As such, pressure sensor P2 is located in a pocket that generally contains aqueous—it is in a wet location 410. Pressure sensor P3 is physically separated from pressure sensor P2 by divider 350. Divider 350 is a physical structure that separates the wet location 410 of P2 from the dry location 360 of P3. Divider 350 is included when the system of the present invention is located on a single substrate. In this configuration, all three pressure sensors (P1, P2, and P3) are located on a substrate that includes tube 430, valve 420, divider 350, and the other components of the system.

In one embodiment of the present invention, pressure sensor P3 is located in close proximity to the eye. Pressure sensor P3 may be implanted in the eye under the conjunctiva. In such a case, pressure sensor P3 measures a pressure that can be correlated with atmospheric pressure. For example, true atmospheric pressure can be a function of the pressure reading of pressure sensor P3. P3 may also be located in a dry portion 360 of the subconjunctival space, separate from the drainage location. Regardless of location, pressure sensor P3 is intended to measure atmospheric pressure in the vicinity of the eye or at the eye's surface.

Generally, IOP is a gauge pressure reading—the difference between the absolute pressure in the eye (as measured by P1) and atmospheric pressure (as measured by P3). Atmospheric pressure, typically about 760 mm Hg, often varies in magnitude by 10 mmHg or more. In addition, the effective atmospheric pressure can vary significantly—in excess of 100 mmHg—if a patient goes swimming, hiking, riding in airplane, etc. Such a variation in atmospheric pressure is significant since IOP is typically in the range of about 15 mm Hg. Thus, for 24 hour monitoring of IOP, it is desirable to have pressure readings for the anterior chamber (as measured by P1) and atmospheric pressure in the vicinity of the eye (as measured by P3).

Therefore, in one embodiment of the present invention, pressure readings are taken by P1 and P3 simultaneously or nearly simultaneously over time so that the actual IOP can be calculated (as P1−P3 or P1−f(P3)). The pressure readings of P1 and P3 can be stored in memory 220 by processor 215. They can later be read from memory so that actual IOP over time can be interpreted by a physician.

Pressure sensors P1, P2, and P3 can be any type of pressure sensor suitable for implantation in the eye. They each may be the same type of pressure sensor, or they may be different types of pressure sensors. For example, pressure sensors P1 and P2 may be the same type of pressure sensor (implanted in the eye), and pressure sensor P3 may be a different type of pressure sensor (in the vicinity of the eye).

Figure 4:
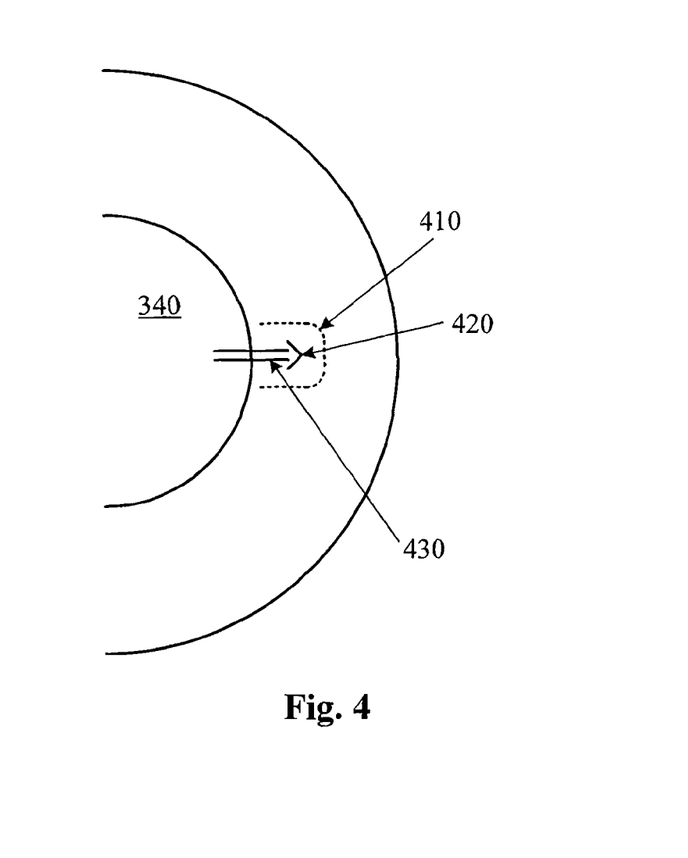
FIG. 4 is a diagram of one possible application of the IOP sensor of the present invention.

In another embodiment of the present invention, pressure readings taken by pressure sensors P1 and P2 can be used to control a device that drains aqueous from the anterior chamber 340. FIG. 4 is a diagram of one possible application of the IOP sensor of the present invention that utilizes the readings of pressures sensors P1 and P2. In FIG. 4, pressure sensor P1 measures the pressure in the anterior chamber 340 of the eye. Pressure sensor P2 measures the pressure at a drainage site 410.

Numerous devices have been developed to drain aqueous from the anterior chamber 340 to control glaucoma. Most of these devices are variations of a tube that shunts aqueous from the anterior chamber 340 to a drainage location 410. For example, tubes have been developed that shunt aqueous from the anterior chamber 340 to the subconjunctival space thus forming a bleb under the conjunctiva or to the subscleral space thus forming a bleb under the sclera. (Note that a bleb is a pocket of fluid that forms under the conjunctiva or sclera). Other tube designs shunt aqueous from the anterior chamber to the suprachoroidal space, the supraciliary space, the juxtauveal space, or to the choroid. In other applications, tubes shunt aqueous from the anterior chamber to Schlemm's canal, a collector channel in Schlemm's canal, or any of a number of different blood vessels like an episcleral vein. Some tubes even shunt aqueous from the anterior chamber to outside the conjunctiva. Finally, in some applications, no tube is used at all. For example, in a trabeculectomy (or other type of filtering procedure), a small hole is made from the subconjunctival or subscleral space to the anterior chamber. In this manner, aqueous drains from the anterior chamber, through the hole, and to a bleb under the conjunctiva or sclera. Each of these different anatomical locations to which aqueous is shunted is an example of a drainage location 410.

In FIG. 4, a tube 430 with a valve 420 on one end is located with one end in the anterior chamber 340 and the other end in a drainage location 410. In this manner, the tube 430 drains aqueous from the anterior chamber 340 to the drainage location 410. Valve 420 controls the flow of aqueous from anterior chamber 340 to drainage location 410. Pressure sensor P1 is located in the anterior chamber or in fluid communication with the anterior chamber 340. As shown in the embodiment of FIG. 3, pressure sensor P1 is located upstream from valve 420. In this manner, pressure sensor P1 is located in the subconjunctival space but is in fluid communication with the anterior chamber 340.

Since pressure sensor P1 measures the pressure in the anterior chamber 340 and pressure sensor P2 measures pressure at the drainage location 410, the difference between the readings taken by these two pressure sensors (P1-P2) provides an indication of the pressure differential between the anterior chamber 340 and the drainage location 410. In one embodiment, this pressure differential dictates the rate of aqueous flow from the anterior chamber 340 to the drainage location 410.

One complication involved with filtering surgery that shunts the anterior chamber 340 to a drainage location 410 is hypotony—a dangerous drop in IOP that can result in severe consequences. It is desirable to control the rate of aqueous outflow from the anterior chamber 340 to the drainage location 410 so as to prevent hypotony. Readings from pressure sensor P1 and pressure sensor P2 can be used to control the flow rate through tube 430 by controlling valve 420. For example, valve 420 can be controlled based on the pressure readings from pressure sensor P1 and pressure sensor P2.

In another embodiment of the present invention, IOP (based on readings from pressure sensor P1 and pressure sensor P3) can be controlled by controlling valve 420. In this manner, IOP is the control parameter. Valve 420 can be adjusted to maintain a particular IOP (like an IOP of 15 mm Hg). Valve 420 may be opened more at night than during the day to maintain a particular IOP. In other embodiments, an IOP drop can be controlled. Immediately after filtering surgery, IOP can drop precipitously. Valve 420 can be adjusted to permit a gradual drop in IOP based on readings from pressure sensors P1 and P3.

In another embodiment of the present invention, readings from pressure sensor P2 (or from the difference between pressure sensor P2 and atmospheric pressure as measured by P3) can be used to control valve 420 so as to control the morphology of a bleb. One of the problems associated with filtering surgery is bleb failure. A bleb can fail due to poor formation or fibrosis. The pressure in the bleb is one factor that determines bleb morphology. Too much pressure can cause a bleb to migrate to an undesirable location or can lead to fibrosis. The pressure of the bleb can be controlled by using the reading from pressure sensor P2 (at drainage location 410—in this case, a bleb). In one embodiment of the present invention, the difference between the pressure in the bleb (as measured by P2) and atmospheric pressure (as measured by P3) can be used to control valve 420 to maintain a desired bleb pressure. In this manner, the IOP pressure sensor of the present invention can also be used to properly maintain a bleb.

Valve 420 can be controlled by microprocessor 215 or a suitable PID controller. A desired pressure differential (that corresponds to a desired flow rate) can be maintained by controlling the operation of valve 420. Likewise, a desired IOP, IOP change rate, or bleb pressure can be controlled by controlling the operation of valve 420.

While valve 420 is depicted as a valve, it can be any of a number of different flow control structures that meter, restrict, or permit the flow of aqueous from the anterior chamber 340 to the drainage location 410. In addition, valve 420 can be located anywhere in or along tube 430.

Finally, there are many other similar uses for the present IOP sensor. For example, various pressure readings can be used to determine if tube 420 is occluded or obstructed in some undesirable manner. As such, failure of a drainage device can be detected. In a self clearing lumen that shunts the anterior chamber 340 to a drainage location 410, an undesirable blockage can be cleared based on the pressure readings of P1, P2, and/or P3.

Figure 5:
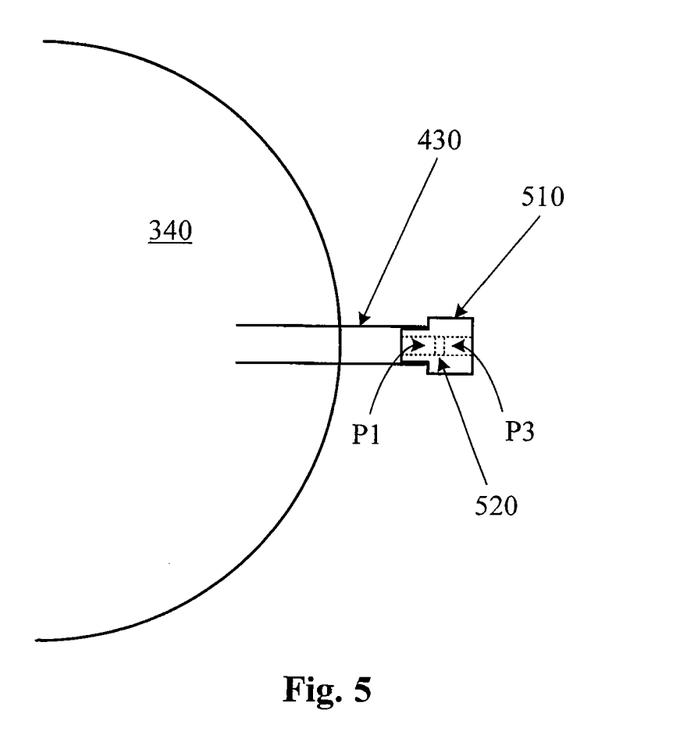
FIG. 5 is an end cap implementation of an IOP sensor consistent with the principles of the present invention.

FIG. 5 is an end cap implementation of an IOP sensor consistent with the principles of the present invention. In FIG. 5, pressure sensors P1 and P3 are integrated into an end cap 510. End cap 510 fits in tube 430 so as to form a fluid tight seal. One end of tube 430 resides in the anterior chamber 340, and the other end of tube 430 (where end cap 510 is located) is located outside of the anterior chamber 340. Typically, on end of tube 430 resides in the anterior chamber 340, and the other end resides in the subconjunctival space. In this manner, pressure sensor P1 is in fluid communication with the anterior chamber 340. Since there is almost no pressure difference between the anterior chamber 340 and the interior of tube 430 that is in fluid contact with the anterior chamber 340, pressure sensor P1 measures the pressure in the anterior chamber 340. Pressure sensor P3 is external to the anterior chamber 340 and either measures atmospheric pressure or can be correlated to atmospheric pressure.

Typically, tube 430 is placed in the eye to bridge the anterior chamber 340 to the subconjunctival space, as in glaucoma filtration surgery. In this case, P3 resides in the subconjunctival space. In this configuration, P3 measures a pressure that is either very close to atmospheric pressure or that can be correlated to atmospheric pressure through the use of a simple function. Since plug 510 provides a fluid tight seal for tube 430, pressure sensor P3 is isolated from pressure sensor P1. Therefore, an accurate IOP reading can be taken as the difference between the pressure readings of P1 and P3 (P1-P3). In one embodiment, a single, thin membrane 520—typically a piezoresistive crystal—resides in the sensor package and is exposed to P1 on one side (tube side) and P3 on the other side (isolation side), and thus the net pressure on the membrane 520 is recorded by the sensor, providing a gauge reading corresponding IOP.

Figure 6A:
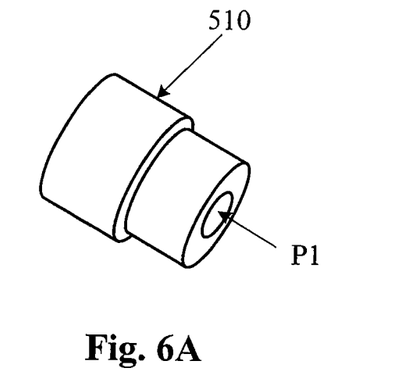
FIGS. 6A and 6B are perspective views of an end cap implementation of an IOP sensor consistent with the principles of the present invention.
Figure 6B:
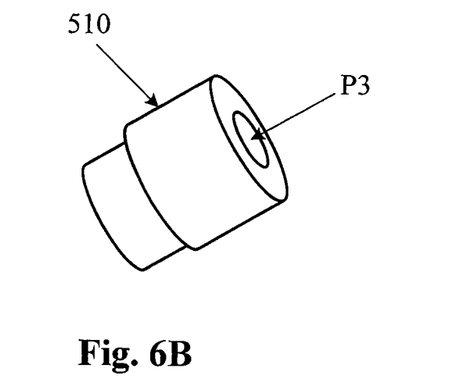

FIGS. 6A and 6B are perspective views of the end cap implementation of FIG. 5. In this embodiment, pressure sensor P1 is located on one end of end cap 510 so that it can be located inside tube 430. Pressure sensor P3 is located on the other end of end cap 510 so that it can be located outside of tube 430. A membrane (520) separates P1 from P3. In this manner, pressure sensor P1 is isolated from pressure sensor P3. While pressure sensors P1 and P3 are depicted as being located on opposite surfaces of a membrane 520 in the end cap 510, they can also be located integral with end cap 510 in any suitable position to facilitate the pressure measurements.

Figure 7A:
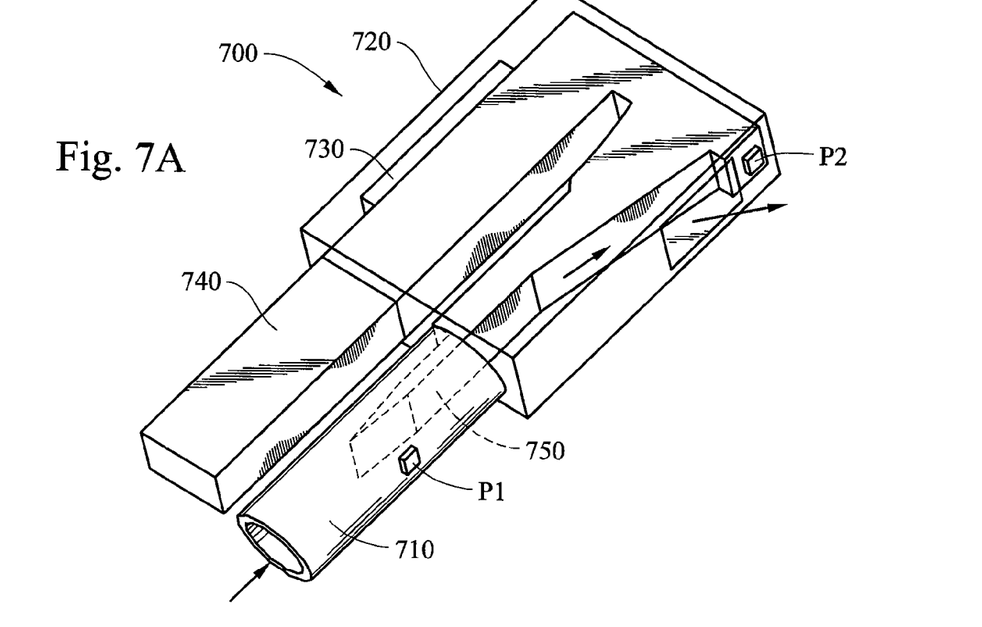
FIGS. 7A and 7B are perspective views of a lumen clearing valve according to the principles of the present invention.
Figure 7B:
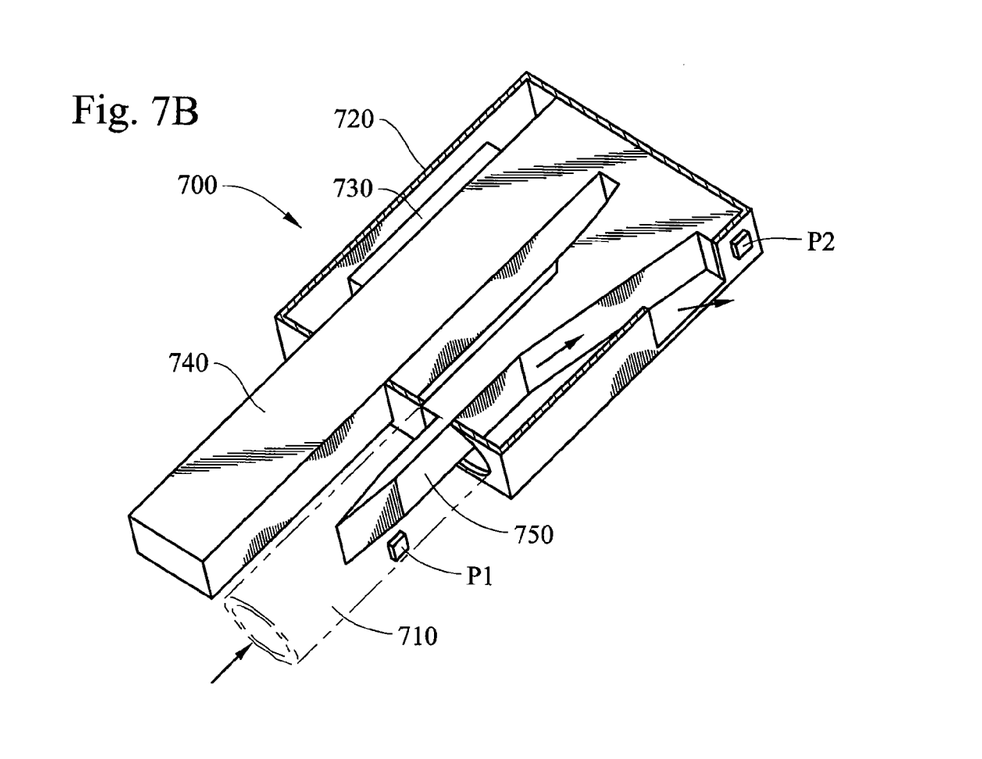

FIGS. 7A and 7B are perspective views of a lumen clearing valve according to the principles of the present invention, which can serve as control valve 420. In FIGS. 7A and 7B, the lumen clearing valve 700 includes tube 710, housing 720, actuator 730, actuation arm 740, tapered arm 750, pressure sensor P1, and pressure sensor P2. As previously described with reference to FIGS. 3 and 4, one end of tube 710 is located in the anterior chamber and the other end of tube 710 is coupled to housing 720. Pressure sensor P1 is located in the anterior chamber. Actuator 730 is located in housing 720. Actuator 730 is coupled to actuation arm 740 which in turn is rigidly connected to tapered arm 750. Tapered arm 750 is configured to extend into the lumen of tube 710. Pressure sensor P2 is located at the outflow region of housing 720 (i.e. in the drainage location). The arrows denote the flow of aqueous from the anterior chamber to the drainage location.

Housing 720 is generally flat but may have a slight curvature that accommodates the curvature of the eye. Housing 720 holds actuator 730. Housing 720 also holds the actuation arm 740 and tapered arm 750. Tube 710 is fluidly coupled to a channel located in the interior of housing 720. This channel conducts aqueous from the anterior chamber (through tube 710) and to the drainage location. Housing 720 can be made of any of a number of different biocompatible materials such as stainless steel.

Actuator 730 moves actuation arm 740 back and forth in a plane. In this manner, actuation arm 740 oscillates or reciprocates when a force is applied on it by actuator 730. Since tapered arm 750 is rigidly coupled to actuation arm 740, it also oscillates or reciprocates in tube 710. Actuator 730 can be based any of a number of different known methods such as electromagnetic actuation, electrostatic actuation, piezoelectric actuation, or actuation by shape memory alloy materials. Actuation arm 740 can be moved by actuator 730 at a low repetition rate (for example, a few Hertz) or a high actuation rate (for example, ultrasonic).

Tapered arm 750 is sized to fit in tube 710. In this manner, tapered arm 750 can be made to oscillate back and forth in tube 710 to clear any material that is blocking tube 710. Tapered arm 750 has a generally pointed end that is located in tube 710. As shown, tapered arm 750 also has a larger tapered portion that can serve to restrict flow through tube 710 thus functioning as a valve. In this manner, not only can tapered arm 750 be oscillated to clear material blocking tube 710, but it can also be moved to a position that partially obstructs flow through tube 710. The tapered designed of arm 750 allows for a variable level of flow restriction through tube 710 by the varying the position of arm 750 relative to housing 720 and tube 710.

When used as a valve, tapered arm 750 can restrict the amount of aqueous that enters the drainage location and exits the anterior chamber. Controlling aqueous flow can reduce the chances of hypotony after filtration surgery, maintain a suitable IOP, and control the amount of stagnant aqueous in the drainage location. When the drainage location is a subconjunctival bleb, controlling the amount of stagnant aqueous in the bleb can help maintain proper bleb morphology and reduce the amount of fibrosis. Too much stagnant aqueous in a bleb can lead to fibrosis. It has been postulated that fibroblasts form in stagnant aqueous and that too much tension on the bleb wall (i.e. too high a pressure in the bleb) can lead to bleb failure. The use of tapered arm 750 as a valve, therefore, can lead to proper bleb maintenance which decreases the chances of these deleterious side effects.

The lumen clearing valve system 700 can be controlled based on readings from P1, P2, and P3 as described above. The lumen clearing valve system 700 of the present invention can be made using a MEMS process in which layers are deposited on a substrate that forms part of housing 720. All of the elements of the lumen clearing valve system 700 can be located on, under, or embedded in a plate that extends into the drainage location—much like currently available glaucoma drainage devices.

Figure 8:
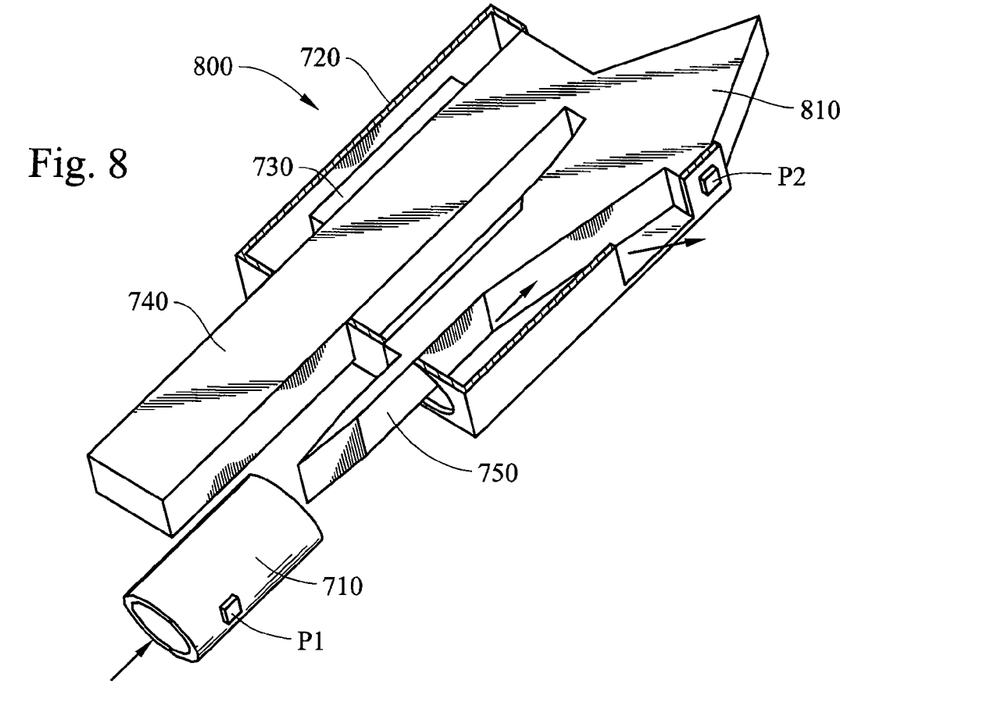
FIG. 8 is a perspective view of a lumen clearing valve with a fiber clearing member according to the principles of the present invention.

FIG. 8 is a perspective view of a lumen clearing valve with a fiber clearing member according to the principles of the present invention. The embodiment of FIG. 8 is similar to that of FIG. 7, except that FIG. 8 also depicts a needle head 810 that is located in the drainage location. Typically, the drainage location is in the subconjunctival space. In this manner, a bleb in the subconjunctival space receives the aqueous that exits the housing 710. Needle head 810 can be oscillated to keep the bleb clear of fibers or to reduce fibrosis (which is one cause of bleb failure). In this manner, when actuation arm 740 is moved, needle head 810 is moved in the drainage location (in this case, a bleb). Needle head 810 can dislodge fibers and prevent the build up of fibrotic tissue.

Figure 9:
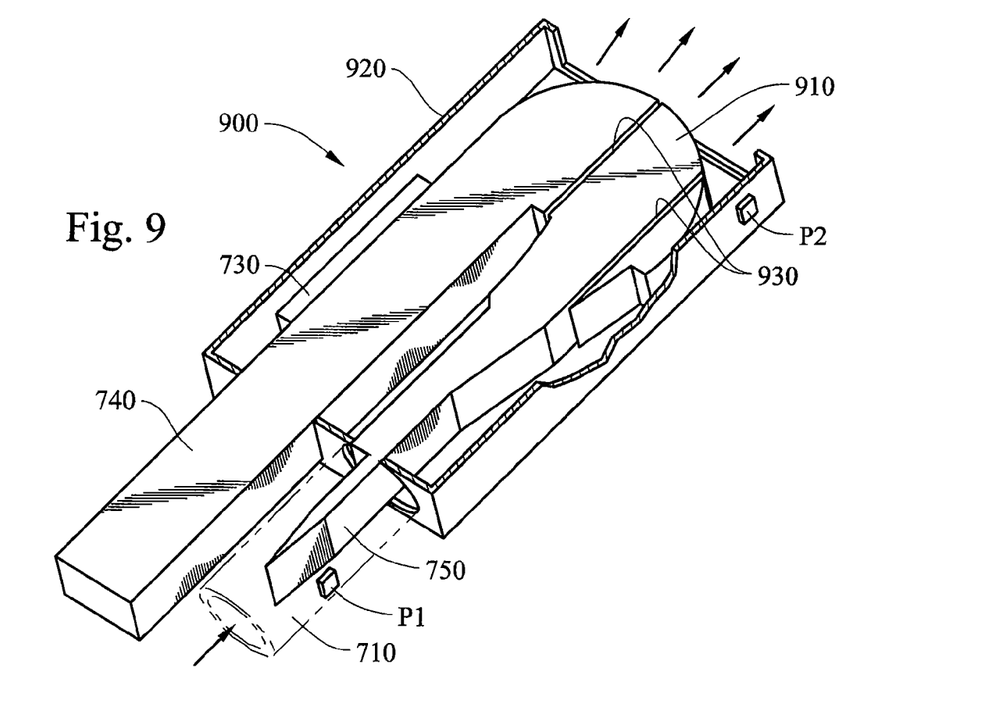
FIG. 9 is a perspective view of a lumen clearing valve with an aqueous dispersion member to clear fibrosis according to the principles of the present invention.

FIG. 9 is a perspective view of a lumen clearing valve with an aqueous dispersion member to clear fibrosis according to the principles of the present invention. The embodiment of FIG. 9 is similar to that of FIG. 7, except that FIG. 9 also depicts a needle head 910 that is located in the drainage location. In this embodiment, needle head 910 may serve to clear fibers in the drainage location and/or disperse aqueous to the drainage location. The outlet end of housing 920 is open to allow aqueous to flow to the drainage location. Needle head 910 is located near the outlet within the housing. Needle head 910 is generally broad and blunt so that when it oscillates, aqueous is distributed to the drainage location. Fluid passes from tube 710 to the drainage location via microchannels 930, which are typically etched into needle head 910. The dispersion of aqueous can help reduce the formation of resistance at the drainage location, typically created by bleb formation and/or fibrotic growth, by providing a larger effective area in the drainage location, decreasing bleb height, and/or reducing bleb pressure in order to more properly manage bleb morphology. Additionally, the dispersion of aqueous can aid the flow of drainage by providing a mechanical means of overcoming the flow resistance associated with the drainage location, typically created by bleb formation and/or fibrotic growth.

Figure 10:
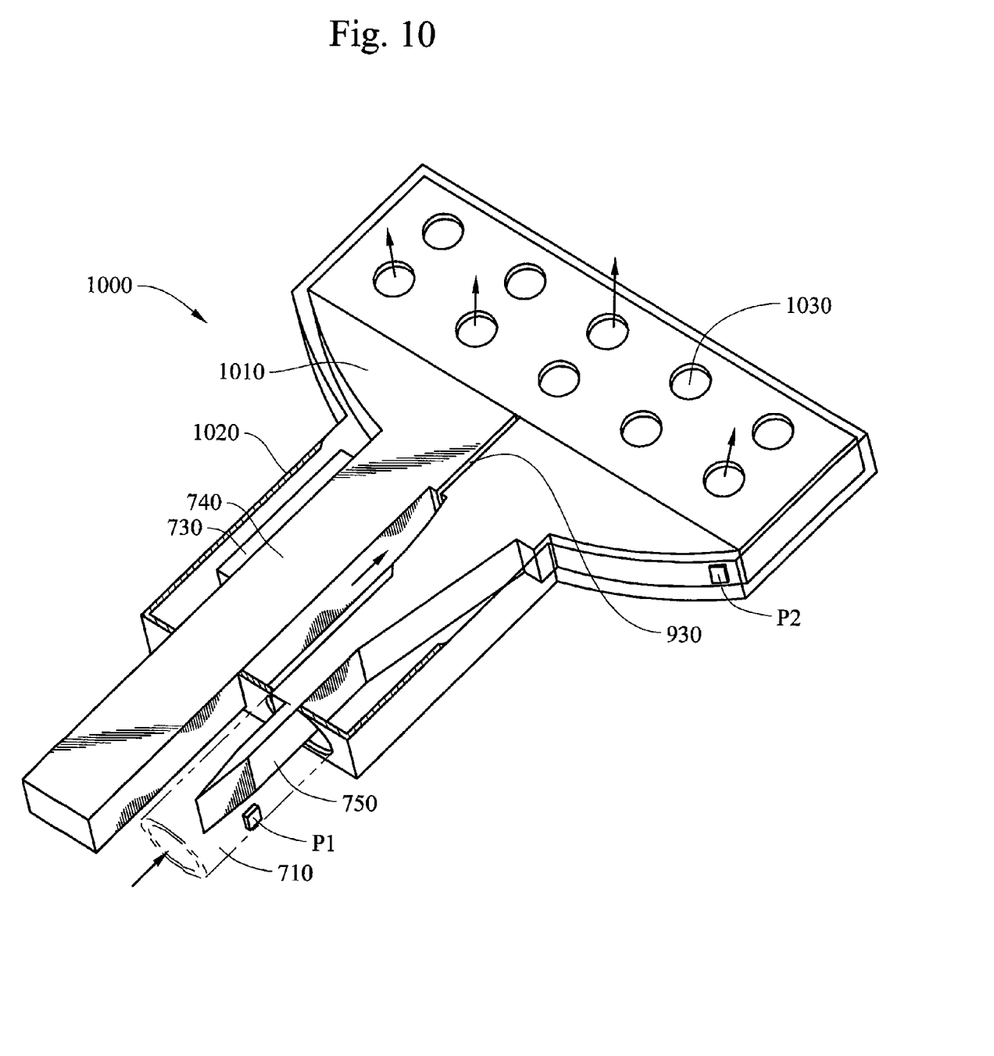
FIG. 10 is a perspective view of a lumen clearing valve with hybrid external member according to the principles of the present invention.

FIG. 10 is a perspective view of a lumen clearing valve with hybrid external member according to the principles of the present invention. The embodiment of FIG. 10 is similar to the embodiment of FIG. 9. In FIG. 10, a broad needle head 1010 and additional drainage holes 1030 allow for a wide dispersion of aqueous in the drainage location (typically, a subconjunctival bleb). Fluid passes from tube 710 to the drainage location via microchannels 930, which are typically etched into needle head 1010. In FIG. 10, housing 1020 has a broad outlet end that includes multiple drainage holes 1030. In addition, the broad end of housing 1020 is open to allow aqueous to flow through this wide opening. Therefore, in the embodiment of FIG. 10, aqueous flows from the anterior chamber through tube 710, through housing 1020 and out of drainage holes 1030 and the broad end of housing 1020 into the drainage location. When needle head 1010 is oscillated, it can serve to clear fibers from the drainage location. It can also disperse aqueous to the drainage location.

The embodiments of FIGS. 7-10 can be operated in two different modes—lumen clearing mode in which the tapered arm 750 oscillates or moves and valve mode in which the tapered arm 750 is maintained in a particular position to restrict fluid flow through tube 710. In lumen clearing mode, tapered arm 750 is moved or oscillated to clear fibrous material from the interior of tube 710 and/or the drainage location. In lumen clearing mode, tapered arm 750 can also help to disperse aqueous in the drainage location.

When operating as a valve, tapered arm 750 can be maintained in a particular position to restrict the flow of aqueous through tube 710. The position of tapered arm 750 can be changed over time based on pressure readings from pressure sensors P1, P2, and/or P3 as described above with respect to FIGS. 3-6. In this manner, any of the following can be the basis for control of the tapered arm 750: IOP, pressure in the bleb, fluid flow rate, etc.

Figure 11A:
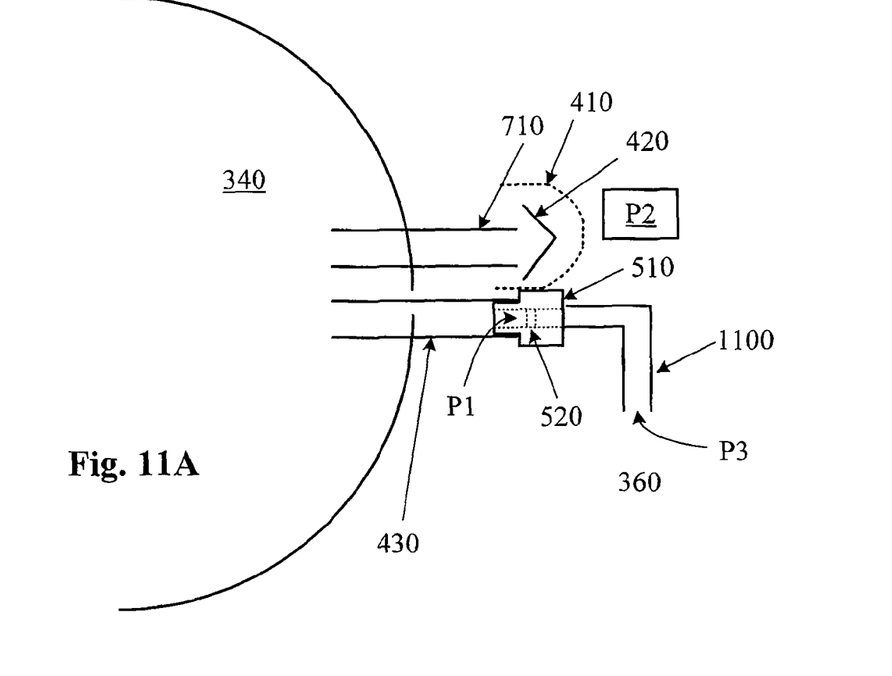
FIGS. 11A and 11B depict an end cap implementation of the valve and pressure sensor system according to the principles of the present invention that includes both single and dual lumen versions.
Figure 11B:
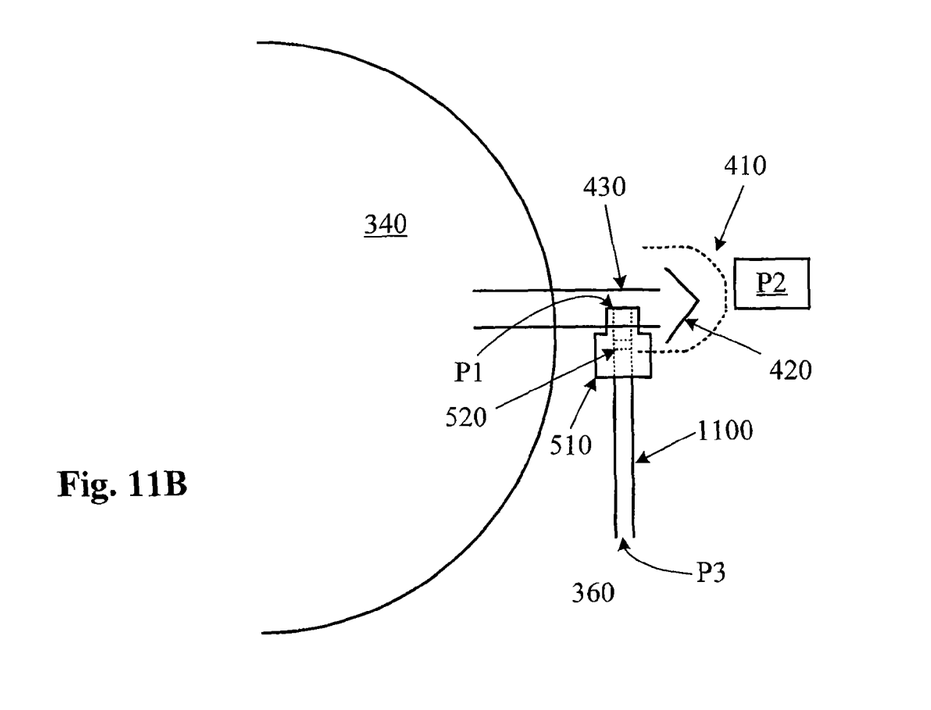

FIG. 11A is a diagram of a two lumen valve and pressure sensor system according to the principles of the present invention. In FIG. 11A, tube 710 of the active valve/lumen clearing system bridges the anterior chamber and a drainage location. A second tube 430 includes end cap 510 as described in FIG. 5. The system of FIG. 11A combines the pressure sensor of FIGS. 5 and 6 with the active valve/lumen clearing device of FIGS. 7-10, wherein the latter can serve as control valve 420. In this manner, one tube (430) can be used to measure IOP, while a second tube (710) can be used for draining aqueous. Fluidic communication between a dry location 360 and the P3 sensing portion of end cap 510 can be provided by tube 1100. FIG. 11B is another possible arrangement, wherein a single tube resides in the anterior chamber 340. In FIG. 11B, end cap 510 is located in an opening in tube 430.

Figure 12A:
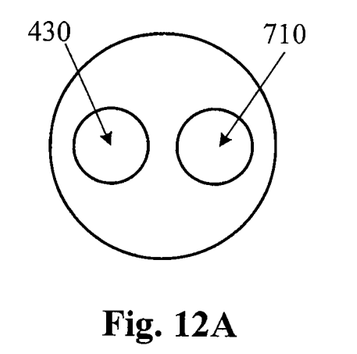
FIGS. 12A and 12B are cross section views of dual tubing that can be used with the system of the present invention.
Figure 12B:
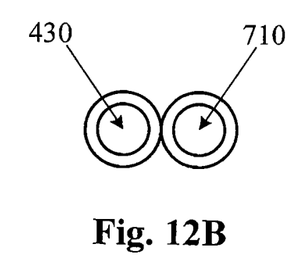

FIGS. 12A and 12B are cross section views of dual tubing that can be used with the system of the present invention. In FIG. 12A, two lumens, 430 and 710, are contained in a single tube. FIG. 12A shows this dual bore tubing arrangement. In FIG. 12B, two lumens, 430 and 710, are contained in two separate tubes that are joined together. FIG. 12B shows this dual-line tubing arrangement. Other variations of a dual lumen device can also be used in conjunction with the present invention.

Figure 13:
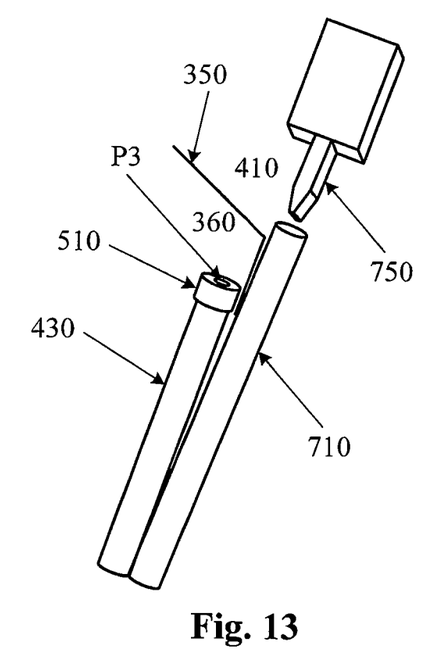
FIG. 13 is a perspective view of a two lumen valve and pressure sensor system according to the principles of the present invention.

FIG. 13 is a perspective view of a two lumen valve and pressure sensor system according to the principles of the present invention. In FIG. 13, two tunes, 430 and 710, are connected at one end (the end that resides in the anterior chamber) and are separated at the other end (in this case, the end that resides in the subconjunctival space). Tube 430 has end cap 510 that measures IOP. Tube 710 receives tapered arm 750. Tapered arm 750 can serve to clear the interior of tube 710. Tube 750 can also act as a valve that can partially or totally occlude the interior of tube 710. Tapered arm 750 is coupled to the any of the systems depicted in FIGS. 7-10. A barrier 350 separates P3 from the outlet of 710, typically the drainage location 410. In this manner, P3 is in a "dry" space 360 and measures an approximation of atmospheric pressure. The outlet end of 710 (shown adjacent to tapered arm 750) is located in a "wet" space or drainage location such as 410. As noted above, P2 is located in this "wet" space.

From the above, it may be appreciated that the present invention provides a lumen clearing valve that can be controlled by an IOP sensor. The present invention provides a valve-like device that can clear a lumen, disperse aqueous, and/or clear fibrous material from a drainage location. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A glaucoma drainage device comprising:
   a housing with an open outlet end;
   a tube in fluid communication with the housing;
   a continuous lumen extending through the tube and the housing;
   an actuator located in the housing;
   an actuation arm located at least partially in the housing, the actuation arm coupled to the actuator; and
   a tapered arm rigidly coupled to the actuation arm, a tapered end of the tapered arm located at least partially in the lumen.

2. The glaucoma drainage device of claim 1 wherein when the actuator moves the actuation arm and tapered arm, the tapered arm moves within the tube thereby clearing the tube.

3. The glaucoma drainage device of claim 1 wherein the tapered arm partially obstructs the lumen thereby restricting fluid flow through the tube.

4. The glaucoma drainage device of claim 1 wherein a first end of the tube is located in an anterior chamber of an eye and the outlet end of the housing is located in a subconjunctival space of the eye.

5. The glaucoma drainage device of claim 1 further comprising:
   drainage holes located on the outlet end of the housing.

6. The glaucoma drainage device of claim 1 further comprising:
   a needle head connecting the actuation arm to the tapered arm, the needle head located opposite the tapered end of the tapered arm.

7. The glaucoma drainage device of claim 6 wherein the actuator moves the needle head in a drainage location to clear fibers from the drainage location.

8. The glaucoma drainage device of claim 7 wherein the drainage location is a bleb.

9. The glaucoma drainage device of claim 6 wherein the actuator moves the needle head in a drainage location to disperse aqueous in the drainage location.

10. The glaucoma drainage device of claim 1 wherein the housing, the tube, the actuator, the actuation arm, and the tapered arm are located on or embedded in a substrate.

11. The glaucoma drainage device of claim 1 further comprising:
    a first pressure sensor located in fluid communication with an anterior chamber of an eye; and
    a second pressure sensor located in the vicinity of the outlet end of the housing;
    wherein a difference between readings from the first pressure sensor and the second pressure sensor approximates a pressure differential between the anterior chamber and the drainage location.

12. The glaucoma drainage device of claim 11 further comprising:
    a controller configured to control a position of the tapered arm based on the readings from the first pressure sensor and the second pressure sensor.

13. The glaucoma drainage device of claim 12 wherein a substantially constant pressure differential is maintained by controlling the position of the tapered arm.

14. The glaucoma drainage device of claim 13 wherein the pressure differential is adjusted by controlling the position of the tapered arm.

15. The glaucoma drainage device of claim 1 further comprising:
    a first pressure sensor located in fluid communication with an anterior chamber of an eye; and
    a remote pressure sensor located remotely from the first pressure sensor such that the remote pressure sensor measures or approximates atmospheric pressure
    wherein a difference between readings from the first pressure sensor and the remote pressure sensor approximates intraocular pressure.

16. The glaucoma drainage device of claim 15 wherein the remote pressure sensor is located in a subconjunctival space of the eye.

17. The glaucoma drainage device of claim 15 further comprising:
    a barrier that separates the first pressure sensor from the remote pressure sensor.

18. The glaucoma drainage device of claim 15 further comprising:
    a controller configured to control a position of the tapered arm based on the readings from the first pressure sensor and the remote pressure sensor.

19. The glaucoma drainage device of claim 18 wherein a substantially constant intraocular pressure is maintained in the eye by controlling the position of the tapered arm.

20. The glaucoma drainage device of claim 18 wherein a substantially constant intraocular pressure drop is maintained by controlling the position of the tapered arm.

21. The glaucoma drainage device of claim 15 further comprising:
    a second tube with a first end located in the anterior chamber and a second and located outside the anterior chamber; and
    a plug located in the second end of the second tube, the plug having the first pressure sensor on one side of the plug and the remote pressure sensor on the other side of the plug.

22. The glaucoma drainage device of claim 1 further comprising:
    a first pressure sensor located in a drainage location; and
    a remote pressure sensor located remotely from the first pressure sensor such that the remote pressure sensor measures or approximates atmospheric pressure wherein a difference between readings from the first pressure sensor and the remote pressure sensor approximates pressure in the drainage location.

23. The glaucoma drainage device of claim 22 further comprising:
   a barrier that separates the first pressure sensor from the remote pressure sensor.

24. The glaucoma drainage device of claim 22 further comprising:
   a controller configured to control a position of the tapered arm based on the readings from the first pressure sensor and the remote pressure sensor.

25. The glaucoma drainage device of claim 24 wherein a substantially constant pressure is maintained in the drainage location by controlling the position of the tapered arm.

26. The glaucoma drainage device of claim 24 wherein the pressure in the drainage location is adjusted by controlling the position of the tapered arm.

* * * * *